United States Patent [19]

Schickaneder et al.

[11] Patent Number: 4,634,700
[45] Date of Patent: Jan. 6, 1987

[54] 1,3-DIOXOLANYL DERIVATIVES, A PROCESS FOR THEIR PREPARATION, THEIR USE AND PHARMACEUTICAL PREPARATIONS CONTAINING THESE COMPOUNDS

[75] Inventors: Helmut Schickaneder, Eckental; Klaus Höxer, Altdorf; Kurt H. Ahrens, Nuremberg, all of Fed. Rep. of Germany

[73] Assignee: Ludwig Heumann & Co., GmbH, Fed. Rep. of Germany

[21] Appl. No.: 687,297

[22] Filed: Dec. 28, 1984

[30] Foreign Application Priority Data

Feb. 10, 1984 [DE] Fed. Rep. of Germany ....... 3404819

[51] Int. Cl.$^4$ .................... A61K 31/41; C07D 405/14
[52] U.S. Cl. .................................. 514/227; 514/237; 514/252; 544/121; 544/357; 544/359; 544/364; 544/366; 544/367; 544/370
[58] Field of Search ............... 544/121, 357, 359, 364, 544/366, 370, 367; 514/227, 237, 252

[56] References Cited

U.S. PATENT DOCUMENTS

| | | | |
|---|---|---|---|
| 3,027,370 | 3/1962 | Bindler | 564/230 |
| 3,157,695 | 11/1964 | Lafont | 564/230 |
| 4,287,195 | 9/1981 | Heeres | 544/367 |
| 4,402,957 | 9/1983 | Heeres | 544/367 |
| 4,456,605 | 6/1984 | Heeres | 544/367 |
| 4,503,055 | 3/1985 | Heeres | 544/121 |

Primary Examiner—Sidney Marantz
Assistant Examiner—Robert Benson
Attorney, Agent, or Firm—Ostrolenk, Faber, Gerb & Soffen

[57] ABSTRACT

1,3-Dioxolanyl derivatives corresponding to the general formula I

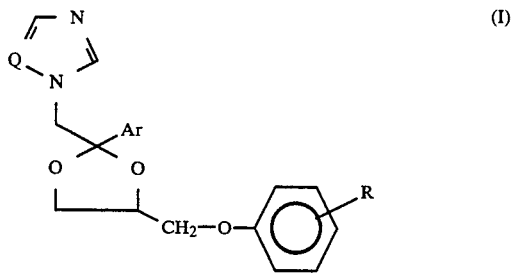

are described. These compounds have an antimicrobial activity and may therefore advantageously be used in chemotherapy.

10 Claims, No Drawings

1,3-DIOXOLANYL DERIVATIVES, A PROCESS FOR THEIR PREPARATION, THEIR USE AND PHARMACEUTICAL PREPARATIONS CONTAINING THESE COMPOUNDS

DESCRIPTION

This invention relates to new 1,3-dioxolanyl derivatives corresponding to the general formula I

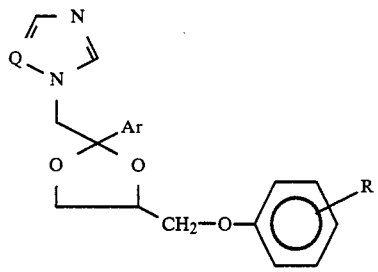

where Q stands for CH or N, and Ar denotes a phenyl group which is unsubstituted or substituted with 1 to 3 halogen atoms. The halogen substituents on the phenyl group may be fluorine, chlorine or bromine atoms, chlorine atoms being preferred. Disubstitution is preferred, disubstitution in the 2- and 4-position being particularly preferred.

The group R has the following meanings:
(a) a group of the general formula II

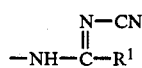

wherein $R^1$ denotes an unsubstituted or substituted amino group, preferably a mono- or disubstituted amino group.

The following are examples of suitable groups for monosubstitution of the amino group: linear, branch chained or cyclic lower alkyl groups, i.e. alkyl groups having 1 to 6, preferably 1 to 3 carbon atoms in the alkyl moiety. Examples are: methyl groups, ethyl groups, propyl groups, isopropyl groups, cyclopentyl groups and cyclohexyl groups, methyl, ethyl, propyl and cyclohexyl groups being preferred. Suitable substituents for disubstitution of the amino group are in particular linear lower alkyl groups having 1 to 6, preferably 1 to 3 carbon atoms in the alkyl moiety, dimethyl groups and diethyl groups being particularly preferred.

$R^1$ may also denote, for example, an optionally substituted pyrrolidine, piperidine, morpholine or piperazine ring. Such a ring is preferably substituted by a methyl group or acetyl group in the 4-position. The unsubstituted pyrrolidine ring and unsubstituted morpholine ring are preferred.

Suitable substituents for monosubstitution of the amino group also include substituted and unsubstituted phenyl and benzyl groups. These are preferably substituted in turn with 1 to 3 haogen atoms, preferably chlorine atoms, in particular with one halogen atom in the 4-position of the aromatic ring.

$R^1$ may also denote a phenoxy group, a linear, branch chained or cyclic alkoxy group, preferably a lower alkoxy group, or a lower thioalkyl group. The term "lower alkoxy groups" is used here to denote groups having 1 to 6, preferably 1 to 3 carbon atoms in the alkyl moiety. The $C_1$ and $C_6$ carbon chain may be interrupted by a built-in oxygen atom to form an alkoxyalkoxy group. The following are examples of such alkoxy groups: methoxy groups, ethoxy groups, propoxy groups, butoxy groups, isopropoxy groups, cyclohexyloxy groups and methoxyethyl groups. The following are preferred: phenoxy groups, methoxy groups, ethoxy groups, propoxy groups, isopropoxy groups and butoxy groups. Thiomethyl and thioethyl groups are examples of lower thioalkyl groups, thiomethyl groups being preferred.

(b) a group of the general formula III

wherein $R^2$ denotes a monosubstituted or disubstituted 5-membered or 6-membered heterocyclic ring system selected from 1,2,4-triazoles, 1,2,4-oxadiazoles and triazines, the heterocyclic residue being attached to the nitrogen atom of the group III by way of a carbon atom.

The amino group and lower alkyl group are suitable substituents, a $C_{1-3}$-alkyl group being preferred.

Thus $R^2$ may represent, for example, a 1,2,4-triazole ring substituted in the 1-position by a hydrogen atom or by lower alkyl groups, preferably methyl or ethyl groups, and in the 3- or 5-position by an amino group.

$R^2$ may also represent, for example, a 1,2,4-oxadiazole ring which is monosubstituted in the 3- or 5-position by an amino group.

A 6-membered heterocyclic ring is preferably a triazine ring disubstituted in the 4- and 6-positions by amino groups.

(c) A group of the general formula IV

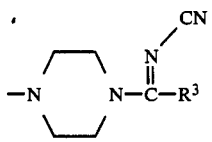

wherein $R^3$ denotes a substituted or unsubstituted amino group or an optionally substituted pyrrolidine, piperidine, morpholine or piperazine ring. Such a ring is preferably substituted in the 4-position by a methyl group or acetyl group. The unsubstituted pyrrolidine and unsubstituted morpholine ring are prefrered.

(d) A group of the general formula V

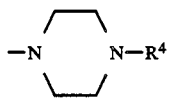

wherein $R^4$ denotes a monosubstituted or disubstituted 5-membered or 6-membered heterocyclic ring selected from 1,2,4-triazoles, 1,2,4-oxadiazoles and triazines, the heterocyclic ring being attached to the nitrogen atom of the piperazine ring by way of a carbon atom.

The invention also covers the physiologically acceptable salts of these new 1,3-dioxolanyl derivatives.

These salts may be formed, for example, with a mineral acid such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methanesulphonic acid, etc.

The invention also includes all tautomeric and isomeric forms and their salts. The compounds according to the invention may form disalts and trisalts and hydrates, and these also fall within the scope of the present invention.

The compounds according to the invention may be prepared as follows:

(a₁) For the preparation of compounds corresponding to the general formula I in which R stands for a group of the general formula II

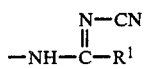  (II)

and R¹ stands for a thiomethyl or phenoxy group, a compound corresponding to the general formula VI

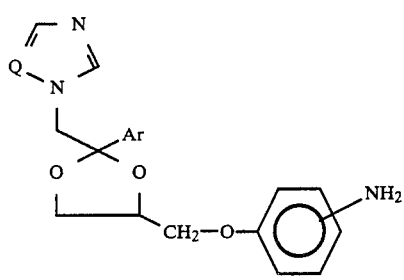  (VI)

is reacted with a compound corresponding to the general formula VII

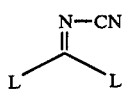  (VII)

wherein L denotes a thiomethyl or phenoxy group as exit group, in a solvent to form a compound according to the invention corresponding to the general formula Ia

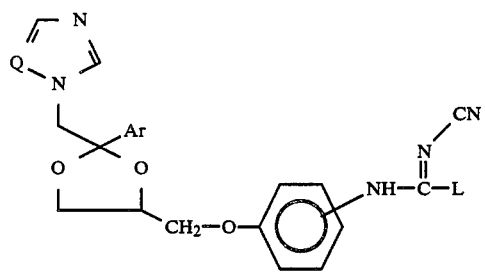  (Ia)

wherein L denotes a thiomethyl or phenoxy group. The reaction is carried out in an inert solvent such as methanol, ethanol or isopropanol, preferably isopropanol, at a temperature ranging from room temperature to the reflux temperature of the solvent and using, for example, equimolar quantities. Compound VI used as starting compound may be prepared in known manner (J.Med.-Chem. 22, 1003 (1979)).

The product is worked up and isolated in the usual manner. The compound obtained may, if desired, be converted into a physiologically acceptable salt thereof.

(a₂) For the preparation of compounds corresponding to the general formula I in which R stands for a group of the general formula II

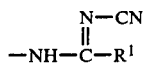  (II)

and R¹ stands for a substituted or unsubstituted amino group,
a compound corresponding to the general formula Ia is reacted with an appropriately substituted amino compound in a solvent. The solvent used may be, for example, an alcohol such as methanol, ethanol or isopropanol, isopropanol being preferred. The reaction is preferably carried out at temperatures from room temperature to the reflux temperature of the solvent used and the reactants may be used, for example, in equimolar quantities.

The product is worked up and isolated in the usual manner. The compound obtained may optionally be converted into a physiologically acceptable salt thereof.

(a₃) For the preparation of compounds corresponding to the general formula I in which R stands for a group of the general formula II

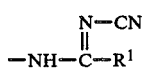  (II)

and R¹ stands for an alkoxy group,
a compound corresponding to the general formula Ia is reacted with an alkali metal alcoholate in the corresponding alcohol as solvent. The reaction is carried out at a temperature from room temperature to the reflux temperature, using, for example, equimolar quantities. The alkali metal alcoholate used is preferably a sodium alcoholate.

The product is worked up and isolated in the usual manner. The compound obtained may optionally be converted into a physiologically acceptable salt thereof.

(a₄) For the preparation of compounds corresponding to the general formula I in which R represents a group of the general formula II

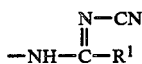  (II)

and R¹ has the meaning indicated above,
a compound corresponding to the general formula VIII

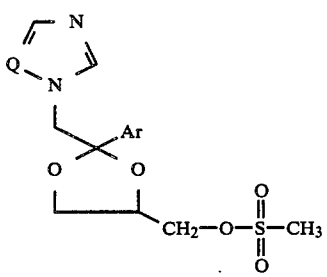  (VIII)

is reacted with a compound corresponding to the general formula IX

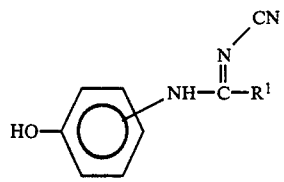 (IX)

wherein $R^1$ has the meaning indicated above. The compound of the general formula VIII used as starting material may be prepared in known manner (J.Med.Chem. 22, 1003 (1979)). The individual reactants are preferably put into the process in equimolar quantities. The reaction is catalysed with a base in a polar aprotic solvent. The bases used may be, for example, sodium hydride or potassium carbonate, sodium hydride being preferred. The bases are preferably used in equimolar quantities. Suitable solvents are, for example, dimethylformamide and dimethylsulphoxide; dimethylformamide is preferred.

The product is worked up and isolated in the usual manner. The compound obtained is optionally converted into a physiologically acceptable salt thereof.

(b₁) For the preparation of compounds corresponding to the general formula I in which R stands for a group of the general formula III

 (III)

and $R^2$ has the meaning indicated above, a compound corresponding to the general formula Ia is reacted with a hydrazine derivative, hydroxylamine or guanidine in a solvent which may be an alcoholic solvent, e.g. methanol, ethanol or isopropanol, preferably ethanol. The reaction is carried out at room temperature to the reflux temperature of the solvent, reflux temperature being preferred.

The product is worked up and isolated in the usual manner. The compound obtained is optionally converted into a physiologically acceptable salt thereof.

(b₂) For the preparation of compounds corresponding to the general formula I in which R stands for a group of the general formula III

 (III)

and $R^2$ has the meaning indicated above,
a compound corresponding to the general formula VIII

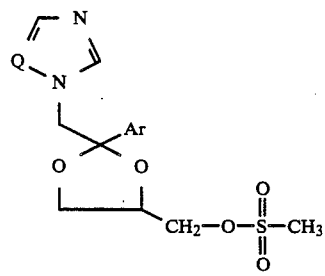 (VIII)

is reacted with a compound corresponding to the general formula X

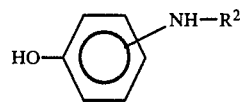 (X)

wherein $R^2$ has the meaning indicated above. The reactants are preferably used in equimolar quantities. The reaction is carried out under the conditions indicated above with reference to process variation a₄).

The product is worked up and isolated in the usual manner. The compound obtained is optionally converted into a physiologically acceptable salt thereof.

(c₁) For the preparation of compounds corresponding to the general formula I in which R stands for a group of the general formula IV

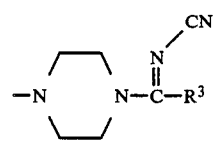 (IV)

and $R^3$ stands for a thiomethyl or phenoxy group, a compound corresponding to the general formula XI

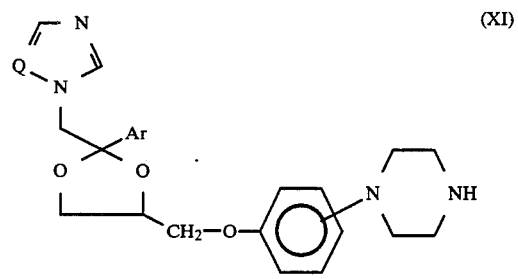 (XI)

is reacted with a compound corresponding to the general formula VII

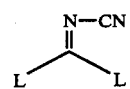 (VII)

wherein L denotes a thiomethyl or phenoxy group as exit group, in a solvent to form the compound according to the invention corresponding to the general formula Ib

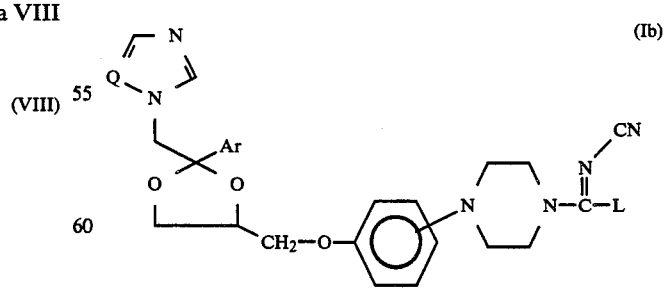 (Ib)

wherein L denotes a thiomethyl or phenoxy group. Compound XI used as starting material may be prepared in known manner (J.Med.Chem. 26, 611 (1983)).

The reaction is carried out in an inert solvent such as methanol, ethanol or isopropanol, preferably isopropanol, and at a temperature from room temperature to the reflux temperature of the solvent used, and the individual reactants may be put into the process, for example, in equimolar quantities.

The product is worked up and isolated in the usual manner. The compound obtained may optionally be converted into a physiologically acceptable salt thereof.

(c₂) For the preparation of compounds corresponding to the general formula I in which R stands for a group of the general formula IV

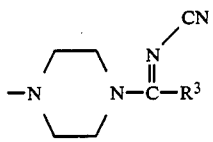

and R³ stands for a substituted or unsubstituted amino group, a compound corresponding to the general formula Ib is reacted with a correspondingly substituted amino compound in a solvent. The solvents used may be alcohols such as methanol, ethanol or isopropanol, the preferred solvent being isopropanol. The reaction is carried out at room temperature to the reflux temperature of the solvent, using equimolar quantities of the starting compounds.

The product is worked up and isolated in the usual manner. The compound obtained may optionally be converted into a physiologically acceptable salt thereof.

(c₃) For the preparation of compounds corresponding to the general formula I in which R stands for a group of the general formula IV and R³ stands for an alkoxy group, a compound corresponding to the general formula Ib is reacted with an alkali metal alcoholate in the corresponding alcohol as solvent. The alkali metal alcoholate used is preferably sodium alcoholate. The reaction is carried out at a temperature from room temperature to the reflux temperature of the solvent and using equimolar quantities of the starting materials.

The product is worked up and isolated in the usual manner. The compound obtained may optionally be converted into a physiologically acceptable salt thereof.

(c₄) For the preparation of compounds corresponding to the general formula I in which R stands for a group of the general formula IV and R³ has the meaning indicated above, a compound corresponding to the general formula VIII

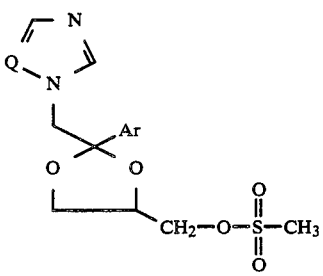

is reacted with a compound corresponding to the general formula XII

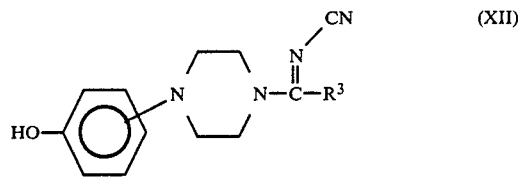

wherein R³ has the meaning indicated above. The reaction is catalysed with a base in a polar aprotic solvent such as dimethylformamide or dimethylsulphoxide, preferably dimethylformamide. The base used may be sodium hydride or potassium carbonate, preferably sodium hydride, and is preferably used in equimolar quantities. The reaction is carried out at a temperature from room temperature to the reflux temperature of the solvent used and preferably with equimolar quantities of the individual starting materials. The product is worked up and isolated in the usual manner. The compound obtained may, if desired, be converted into a physiologically acceptable salt thereof.

(d₁) For the preparation of compounds corresponding to the general formula I in which R stands for a group of the general formula V

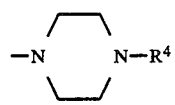

and R⁴ has the meaning indicated above, a compound corresponding to the general formula Ib is reacted with a hydrazine derivative, hydroxylamine or guanidine, in a solvent. The solvent used is preferably an alcohol such as methanol, ethanol or isopropanol, ethanol being preferred, and the reaction temperature may be from room temperature to the reflux temperature of the solvent used, the latter temperature being preferred. The individual reactants are preferably used in equimolar quantities.

The product is worked up and isolated in the usual manner. The compound obtained may, if desired, be converted into a physiologically acceptable salt thereof.

(d₂) For the preparation of compounds corresponding to the general formula I in which R stands for a group of the general formula V and R⁴ has the meaning indicated above, a compound corresponding to the general formula VIII is reacted with a compound corresponding to the general formula XIII

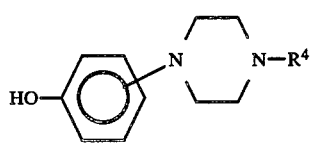

wherein R⁴ has the meaning indicated above. The reaction is preferably carried out under the conditions described above with reference to process variation (d₁).

The product is worked up and isolated in the usual manner. The compound obtained may, if desired, be converted into a physiologically acceptable salt thereof.

The compounds obtained in preparation steps (a₁) to (d₂) may, if desired, be converted into physiologically acceptable salts thereof in known manner. Isolation of the resulting compound corresponding to the general formula I is carried out in conventional manner, for example by crystallisation or column chromatography.

Microbiological investigations

One method of determining the microbiological activity of the compounds according to the invention on yeasts is the determination of the inhibitory concentration 50% (IC 50%). The IC 50% is the concentration of test substance which has inhibited the growth of the test strain by more than 50% in comparison with the untreated control (see J. N. Galgiani, D. A. Stevens; Antimicrob. Agents and Chemoth. 13, 249–254 (1978)).

The microbiological activity is demonstrated in Example 2 in comparison to ketoconazole. The other compounds according to the invention show a similar activity.

TABLE

| | | IC 50% μg/ml | |
|---|---|---|---|
| Strain | pathogen | Example 2 | Keto-conazole |
| Cand. pseudotropicalis | + | 0.00125 | 0.0125 |
| Cand. parapsilosis | + | 0.0125 | 0.0125 |
| Cand. krusei | + | 0.125 | 0.125 |
| Cand. curvata | + | 0.125 | 1.25 |
| Cand. albicans | + | 0.00125 | 0.0125 |
| Sacch. uvarum | (+) | 1.25 | 0.125 |
| Sacch. cerevisiae 1 | (+) | 1.25 | 1.25 |
| Sacch. fragilis | (+) | 0.0125 | 0.0125 |
| Sacch. cerevisiae 2 | (+) | 1.25 | 1.25 |
| Hansenula anomala | − | 0.00125 | 0.125 |
| Cryptococcus neoformans 1 | + | 0.0125 | 0.0125 |
| Cryptococcus neoformans 2 | + | 0.125 | 1.25 |
| Metschnikowia pulch | − | 0.00125 | 0.0125 |
| Sacch. rouxii | (+) | 0.00125 | 0.0125 |
| Geotrichum capitum | + | 0.125 | 1.25 |
| Rhodotorula spec. | − | 1.25 | 1.25 |

The compounds according to the invention, preferably in the form of a salt, may be formulated for administration in any desired manner. The invention therefore also covers medicaments containing at least one compound according to the invention for use in human or veterinary medicine. Such pharmaceutical preparations may be prepared by the conventional methods using one or more pharmacologically acceptable excipients or diluents.

The compounds according to the invention may therefore be formulated for oral, buccal or parenteral administration, oral administration being preferred. For oral administration, the preparation may be, for example, in the form of tablets, capsules, powders, solutions, syrups or suspensions which have been prepared by usual methods using acceptable diluents. For buccal administration, the medicaments may be prepared in the form of tablets for sachets formulated in the usual manner.

The pharmaceutical preparations may assume forms such as suspensions, solutions or emulsions in oily or aqueous vehicles and they may contain formulation auxiliaries such as stabilizers and suspending and/or dispersing agents. Alternatively, the active ingredient may be prepared in powder form to be reconstituted with a suitable vehicle such as sterile, pyrogen-free water before use.

For oral administration, the daily dose of the compounds according to the invention may suitably be given in 1 to 4 doses, preferably 1 or 2 doses, amounting to a total of 50 mg to 500 mg, preferably 100 mg to 250 mg, depending on the condition of the patient.

In some cases, it may be necessary to deviate from the quantities mentioned above, depending on the individual response to the active ingredient or the nature of its formulation or the time at which it is administered or the interval between doses. Thus, for example, in some individual cases less than the above-mentioned minimum quantity may be sufficient whereas in other cases it may be necessary to exceed the upper limit.

EXAMPLE 1 cis-N'-[4-[2-(2,4-Dichlorophenyl)-2-(1H-imidazol-1-ylmethyl)-1,3-dioxolan-4-ylmethoxy]-phenyl]-N''-cyano-methylisothiourea

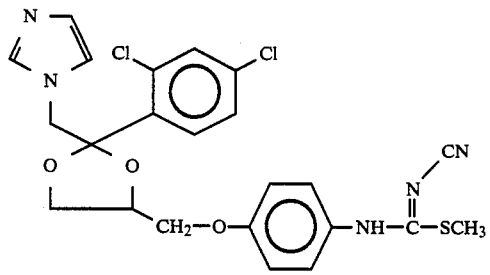
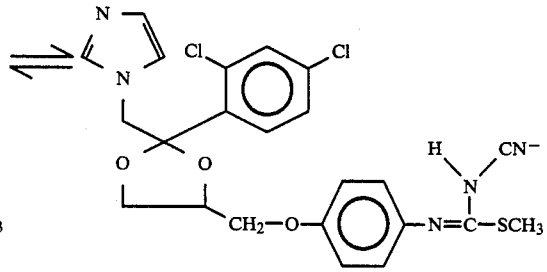

4.2 g (10 mmol) of cis-4-[2-(2,4-Dichlorophenyl)-2-(1H-imidazol-1-ylmethyl)-1,3-dioxolan-4-ylmethoxy]-benzolamine and 1.46 g (10 mmol) of N-cyanodimethyl-dithioimidocarbonate are dissolved in 30 ml of isopropanol and heated to the reflux temperature for 1 hour. The reaction solution is then concentrated by evaporation and the residue is recrystallised from diisopropylether.

Colourless crystals, melting point 90°–92° C. (decomposition)

Rf=0.61 (CH$_2$Cl$_2$/CH$_3$OH 90:10)

Yield: 4.24 g (82% of theoretical)

C$_{23}$H$_{21}$Cl$_2$N$_5$O$_3$S (518) Calculated: C 53.29, H 4.08, N 13.51. Found: C 53.45, H 4.55, N 13.58.

IR (cm$^{-1}$): 2195 (γ-CN)

1$_H$-NMR spectrum (CDCl$_3$, TMS as internal standard): δ=2.47 (s) (SCH$_3$) 3H, 3.13–3.40 (m) (CH) 1H, 3.57–3.97 (m) (CH$_2$, CH) 3H, 4.33 (m) (CH) 1H, 4.40 (s) (CH$_2$) 2H, 6.63–7.67 (m) (aromatic-H, N—H) 11H ppm.

(a) Preparation of N''-cyano-N'-(4-hydroxyphenyl)-methyl isothiourea

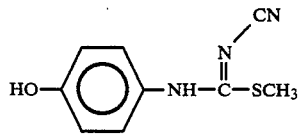

10.9 g (0.1 mol) of 4-hydroxyaniline are reacted with 14.6 g (0.1 mol) of dimethyl-dithio-cyanoimidocarbonate in 60 ml of methanol at 40° C. for 30 minutes. The precipitated solid is suction filtered.

Colourless crystals, melting point 153°–154° C.

Yield: 15.3 g (74% of theoretical)

(b) Preparation of cis-N'-[4-[2-(2,4-dichlorophenyl)-2-(1H-imidazol-1-ylmethyl)-1,3-dioxolan-4-ylmethoxy]-phenyl]-N''-cyano-methylisothiourea 0.425 g (14.8 mmol) of sodium hydride are introduced into 5 ml of anhydrous DMF and reacted for one hour with a solution of 2.8 g (14.8 mmol) of N''-cyano-N'-(4-hydroxyphenyl)-methylisothiourea in 20 ml of anhydrous DMF at room temperature. A solution of 3.0 g (7.4 mmol) of cis-2-(2,4-dichlorophenyl)-2-(1H-imidazole-1-ylmethyl)-1,3-dioxolan-4-yl methyl methane sulphonate and 15 ml of anhydrous DMF is then added dropwise to the reaction mixture and the mixture is heated to 80° C. for 8 hours. After cooling, the reaction solution is concentrated by evaporation under vacuum and the residue is taken up in dichloroethane, the organic phase is extracted with a 2.5% sodium carbonate solution and made neutral with water, and the organic phase is dehydrated over Na2SO4. After concentration of the organic phase, the residue is recrystallised from isopropanol and diisopropylether. The physical data agree with those of Example 1.

EXAMPLE 2 cis-1-Cyanimino-methylthio-methylene-4-[4[[2-(2,4-dichlorophenyl)-2-(1H-imidazol-1-ylmethyl)-1,3-dioxolan-4-yl]-methoxy]-phenyl]-piperazine

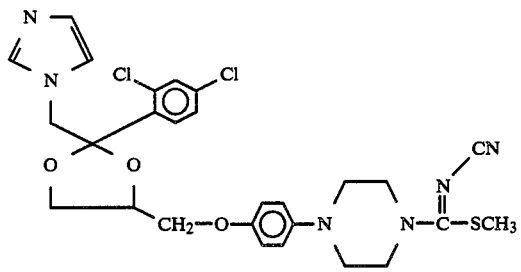

This compound is prepared by a method analogous to that of Example 5b from 4-(4-hydroxyphenyl)-1-(N-cyanimino-methylthiomethylene)-piperazine and cis-2-(2,4-dichlorophenyl)-2-(1H-imidazol-1-ylmethyl)-1,3-dioxolan-4-ylmethyl-methanesulphonate.

Colourless crystals, melting point 142°–144° C.

Rf=0.63 (ethyl acetate/CH3OH 80:20)

$C_{27}H_{28}Cl_2N_6O_3S$ (588) Calculated: C 55.20, H 4.80, N 14.30. Found: C 55.26, H 4.87, N 14.16.

IR (cm$^{-1}$): 2190 (δ-CN)

$^1$H-NMR spectrum (d$_6$-DMSO, TMS as internal standard): δ=2.73 (s) (S—CH$_3$) 3H, 3.13 (m) (2×CH$_2$) 4H, 3.63 (m) (2×CH$_2$) 4H, 3.90 (m) (2×CH$_2$) 4H, 4.33 (m) (CH) 1H, 4.50 (s) (CH$_2$) 2H, 6.70–7.70 (m) (aromatic H) 10H ppm.

EXAMPLE 3 cis-Cyanimino-phenoxy-methylene-4-[4[[2-(2,4-dichlorophenyl)-2-(1H-imidazol-1-ylmethyl)-1,3-dioxolan-4-yl]-methoxy]-phenyl]-piperazine hydrochloride

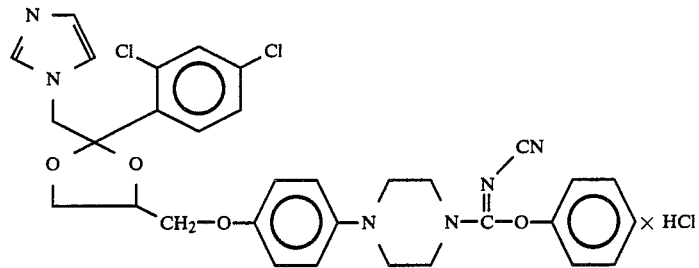

The compound is prepared by a method analogous to that of Example 16 from 4-(4-hydroxyphenyl)-1-(N-cyanimino-phenoxy-methylene)-piperazine and cis-2-(2,4-dichlorophenyl)-2-(1H-imidazol-1-ylmethyl)-1,3-dioxolan-4-ylmethyl-methanesulphonate.

Colourless crystals, melting point 154°–155° C.

Rf=0.47 (diisopropylether/CH3OH 70:30)

$C_{32}H_{31}Cl_3N_6O_4$ (669)

IR (cm$^{-1}$): 2200 (γ-CN)

$^1$H-NMR spectrum (d$_6$-DMSO, TMS as internal standard): δ=3.57 (m) (2×CH$_2$) 4H, 3,87 (m) (2×CH$_2$) 4H, 4.07 (m) (2×CH$_2$) 4H, 4.40 (m) (CH) 1H, 4.87 (s) (CH$_2$) 2H, 6.87–7.80 (m) (aromatic H, —H) 15H, 9.20 (s) (aromatic H) 1H ppm.

EXAMPLE 4 cis-1-[(1-Methyl-3-amino)-1,2,4-triazol-5-yl]-4-[4[[2-(2,4-dichlorophenyl)-2-(1H-imidazol-1-ylmethyl)-1,3-dioxolan-4-yl]-methoxy]phenyl]piperazine

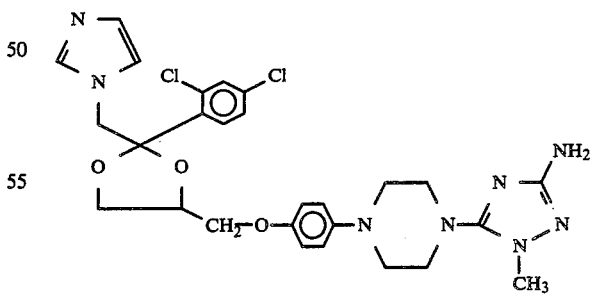

The compound is prepared by a method analogous to that of Example 1b from 4-(4-hydroxyphenyl)-1-(1-methyl-3-amino-1,2,4-triazol-5-yl)-piperazine and cis-2-(2,4-dichlorophenyl)-2-(1H-imidazol-1-ylmethyl)-1,3-dioxolan-4-ylmethyl-methanesulphonate.

Colourless crystals, melting point 194° C.

Rf=0.19 (ethyl acetate/CH3OH 80:20)

$C_{27}H_{30}Cl_2N_8O_3$ (586)

¹H-NMR spectrum (d₆-DMSO, TMS as internal standard): δ=3.13 (m) (2×C$\underline{H}_2$) 4H, 3.43 (s) (CH₃) 3H, 3.63 (m) (2×C$\underline{H}_2$) 4H, 3.87 (m) (2×C$\underline{H}_2$) 4H, 4.33 (m) (C$\underline{H}$) 1H, 4.53 (s) (C$\underline{H}_2$) 2H, 5.00 (broad) (N$\underline{H}_2$) 2H, replaceable by D₂O, 6.67-7.73 (m) (aromatic $\underline{H}$) 10H ppm.

EXAMPLE 5 cis-1-(Cyanimino-methylthio-methylene-4-[4-[[2-(2,4-dichlorophenyl)-2-(1H-1,2,4-triazol-1-ylmethyl)-1,3-dioxolan-4-yl]methoxy]-phenyl]-piperazine

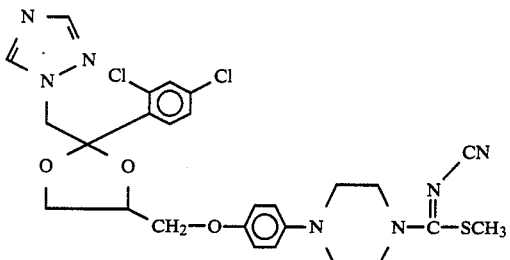

The compound is prepared by a method analogous to that of Example 1b from 4-(4-hydroxyphenyl)-1-(N-cyanimino-methylthiomethylene)-piperazine and cis-(2-(2,4-dichlorophenyl)-2-(1H-1,2,4-triazol-1-ylmethyl)-1,3-dioxolan-4-yl-methyl-methanesulphonate.

Colourless crystals, melting point 67°-68° C.
Rf=0.63 (ethyl acetate/CH₃OH 90:10)
C₂₆H₂₇Cl₂N₇O₃S (588) Calculated: C 53.06, H 4.62, N 16,66. Found: C 53.43, H 4.67, N 16.66.
IR (cm⁻¹): 2190 (γ-CN)
H-NMR spectrum (CDCl₃, TMS as internal standard): δ=2.77 (s) (S—CH₃) 3H, 3.12 (m) (2×C$\underline{H}_2$) 4H, 3.57-4.17 (m) (2×C$\underline{H}_2$, 2×OC$\underline{H}_2$) 8H, 4.37 (m) (C$\underline{H}$) 1H, 4.82 (s) (C$\underline{H}_2$) 2$\underline{H}$, 6.70-7.70 (m) (aromatic $\underline{H}$) 7$\underline{H}$, 7.90 (s) (aromatic $\underline{H}$) 1H, 8.27 (s) (aromatic $\underline{H}$) 1$\underline{H}$ ppm.

EXAMPLE 6 cis-(1-Cyanimino-phenoxy-methylene-4-[4[[2-(2,4-dichlorophenyl)-2-(1H-1,2,4-triazol-1-ylmethyl)-1,3-dioxolan-4-yl]-methoxy]-phenyl]-piperazine

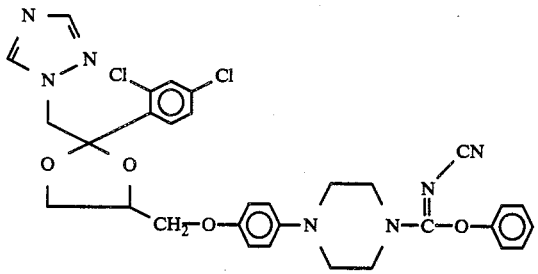

Preparation from 4-(4-hydroxyphenyl)-1-(N-cyaniminophenoxymethylene)-piperazine and cis-2-(2,4-dichlorophenyl)-2-(1H-1,2,4-triazol-1-ylmethyl)-1,3-dioxolan-4-ylmethylmethanesulphonate by a method analogous to that of Example 5b.

Colourless crystals, melting point 129° C.
Rf=0.82 (ethyl acetate/CH₃OH 80:20)
C₃₁H₂₉Cl₂N₇O₄ (635)
IR (cm⁻¹): 2200 (γ-CN)
¹H-NMR spectrum (d₆-DMSO, TMS as internal standard): δ=3.17 (m) (2-C$\underline{H}_2$) 4H, 3.50-4.00 (m) (2×C$\underline{H}_2$, 2×OC$\underline{H}_2$) 8H, 4.32 (m) (C$\underline{H}$) 1H, 4.80 (s) (C$\underline{H}_2$) 2$\underline{H}$, 6.57-7.73 (m) (aromatic $\underline{H}$) 12H, 7.87 (s) (aromatic $\underline{H}$) 1H, 8.40 (s) (aromatic $\underline{H}$) 1H ppm.

EXAMPLE 7 cis-1-Cyanimino-methoxy-methylene-4-[4-[[2-(2,4-dichlorophenyl)-2-(1H-1,2,4-triazol-1-ylmethyl)-1,3-dioxolan-4-yl]-methoxy]-phenyl]-piperazine

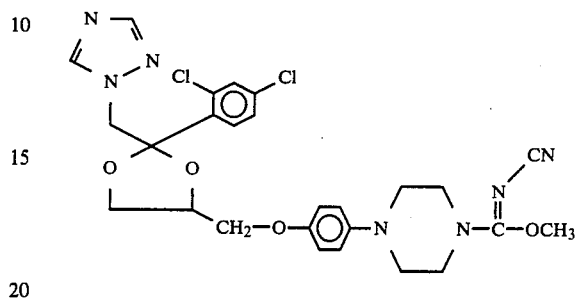

6.35 g (10 mmol) of cis-1-cyanimino-phenoxy-methylene-4-[4[[2-(2,4-dichlorophenyl)-2-(1H-1,2,4-triazol-1-ylmethyl)-1,3-dioxolan-4-yl]methoxy]-phenyl]-piperazine (Example 6) are reacted with 0.57 g (11 mmol) of sodium methylate in 50 ml of methanol at room temperature for 12 hours. After evaporation of solvent, the residue is recrystallised from ethyl acetate.

Colourless crystals, melting point 87°-88° C.
Rf=0.72 (ethyl acetate/CH₃OH 80:20)
C₂₆H₂₇Cl₂N₇O₄ (573) Calculated: C 54.55, H 4.75, N 17.13. Found: C 54.85, H 4.99, N 16.70.
IR (cm⁻¹): 2200 (γ-CN)
¹H-NMR spectrum (d₆-DMSO, TMS as internal standard): δ=3.13 (m) (2×C$\underline{H}_2$) 4H, 3.60-4.11 (m) (2×C$\underline{H}_2$, 2×OC$\underline{H}_2$) 8H, 3.95 (s) (OCH₃) 3H, 4.37 (m) (C$\underline{H}$) 1H, 4.83 (s) (C$\underline{H}_2$) 2H, 6.77-7.80 (m) (aromatic $\underline{H}$) 7$\underline{H}$, 7.93 (s) (aromatic $\underline{H}$) 1H, 8.43 (s) (aromatic $\underline{H}$) 1H ppm.

EXAMPLE 8 cis-1-Cyanimino-methoxy-methylene-4-[4-[[2-(2,4-dichlorophenyl)-2-(1H-imidazol-1-ylmethyl)-1,3-dioxolan-4-yl]-methoxy]-phenyl]-piperazine

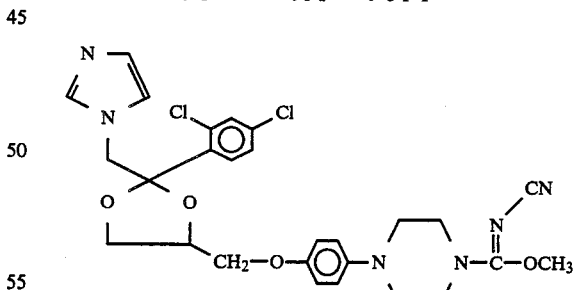

8.0 g (12.6 mmol) of cis-1-cyanimino-phenoxy-methylene-4-[4[[2-(2,4-dichlorophenyl)-2-(1H-imidazol-1-ylmethyl)-1,3-dioxolan-4-yl]methoxy]-phenyl]-piperazine (Example 3) are reacted at room temperature with 2.1 ml (11.5 mmol) of a 5.5 molar sodium methylate solution in 80 ml of methanol for 12 hours. After concentration of the reaction solution by evaporation, the residue is recrystallised from isopropanol/diisopropylether (80:20).

Colourless crystals, melting point 129°-131° C.
Rf=0.6 (ethyl acetate/CH₃OH 80:20)

$C_{27}H_{28}Cl_2N_6O_4$ (572) Calculated: C 56.75, H 4.94, N 14.71. Found: C 56.91, H 5.12, N 14.60.

IR (cm$^{-1}$): 2200 ($\gamma$-CN)

$^1$H-NMR spectrum (CDCl$_3$, TMS as internal standard): δ=3.1 (m) (2×C$\underline{H}_2$) 4H, 3.60–4.07 (m) (2×OC$\underline{H}_2$, 2×C$\underline{H}_2$) 8H, 4.00 (s) (OC$\underline{H}_3$) 3H, 4.37 (m) (C$\underline{H}$) 1$\underline{H}$, 4.43 (s) (C$\underline{H}_2$) 2H, 6.70–7.73 (m) (aromatic $\underline{H}$) 10$\underline{H}$ ppm.

We claim:

1. 1,3-dioxolanyl compound of the formula

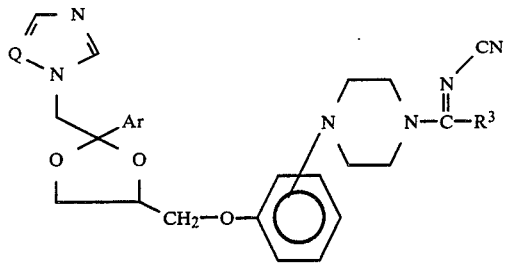

wherein Q is CH or N, Ar is a phenyl group which is unsubstituted or substituted with 1 to 3 halogen atoms and R$^3$ is an amino group, a pyrrolidine, piperidine, morpholine or piperazine ring which is unsubstituted or substituted in the four position by methyl or acetyl, or a lower alkoxy, phenoxy or thio lower alkyl group, and the physiologically acceptable hydrates and salts thereof.

2. A compound according to claim 1 wherein Ar is 2,4-dichlorophenyl and Q is CH.

3. A compound according to claim 2 in which R$^3$ is phenoxy.

4. A compound according to claim 2 in which R$^3$ is —SCH$_3$.

5. A compound according to claim 2 in which R$^3$ is

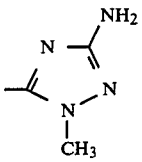

6. Pharmaceutical preparation, characterised in that it contains an antimicrobial effective amount of a compound according to one of claims 1–5, and at least one inert, pharmaceutically acceptable excipient or an inert, pharmaceutically acceptable diluent.

7. A method of combating a microbial infection which comprises administering to a host an antimicrobal effective amount of a compound according to one of claims 1 to 5.

8. The method of claim 7 in which the microbe is mycoses, protozoa and gram positive bacteria.

9. 1-Cyanoimino-methylthio-methyl-4-[4-[[2-(2,4-dichlorophenyl)-2-(1H-imidazol-1-ylmethyl)-1,3-dioxolan-4-yl]-methoxy]-phenyl]-piperazine and its physiologically acceptable acid addition salts.

10. 1-cyanoimino-methoxy-methyl-4-[4[[2-(2,4-dichlorophenyl)-2-(1H-1,2,4-triazol-1-ylmethyl)-1,3-dioxolan-4-yl]-methoxy]-phenyl]-piperazine and its physiological acceptable acid addition salts.

* * * * *